US005260205A

United States Patent [19]

Nakatani et al.

[11] Patent Number: 5,260,205

[45] Date of Patent: Nov. 9, 1993

[54] METHOD OF PURIFYING PUTRESCINE N-METHYLTRANSFERASE FROM TOBACCO PLANT EXTRACT WITH A POLYAMINE

[75] Inventors: Herbert Y. Nakatani, Midlothian; Vedpal S. Malik, Richmond, both of Va.

[73] Assignee: Philip Morris Incorporated, New York, N.Y.

[21] Appl. No.: 613,160

[22] Filed: Nov. 14, 1990

[51] Int. Cl.$^5$ .............................. C12N 9/10
[52] U.S. Cl. ........................... 435/193; 435/815
[58] Field of Search ......................... 435/193, 815

[56] References Cited

U.S. PATENT DOCUMENTS

| | | | |
|---|---|---|---|
| 4,594,319 | 6/1986 | Sharma | 435/7 |
| 4,801,540 | 1/1989 | Hiatt | 435/172.3 |

FOREIGN PATENT DOCUMENTS

| | | |
|---|---|---|
| 0223399 | 5/1987 | European Pat. Off. |
| 0240208 | 7/1987 | European Pat. Off. |
| 0240332 | 7/1987 | European Pat. Off. |
| 0271988 | 6/1988 | European Pat. Off. |

OTHER PUBLICATIONS

Bush and Saunders, "Physiological Aspects Of Genetic Variation In Nicotine Content In Tobacco (*Nicotiana tabacum*)", Tobacco Abstracts, 23, p. 380 (1979).

Bush and Saunders, "Nicotine Biosynthetic Enzymes Of Burley Tobacco", Tobacco Abstracts, 24, p. 260 (1980).

Chung and Blume, "Identification Of Nicotine Biosynthetic Intermediates In Tobacco Roots by Liquid Chromatography-Mass Spectrometry", J. of Chromatography, 474, pp. 329-333 (1989).

Cornelissen and Vandewiele, "Both RNA Level And Translation Efficiency Are Reduced By Anti-Sense RNA In Transgenic Tobacco", Nucleic Acids Res., 17, 3, pp. 833-843 (1989).

Cuozzo et al., "Viral Protection In Transgenic Tobacco Plants Expressing The Cucumber Mosaic Virus Coat Protein Or Its Antisense RNA", Biotechnology, 6, pp. 549-557 (1988).

Davies et al., "Quinoprotein Characteristics Of Methylputrescine Oxidase From Tobacco Roots", Phytochemistry, 28, 6, pp. 1573-1578 (1989).

Delauney et al., "A Stable Bifunctional Antisense Transcript Inhibiting Gene Expression In Transgenic Plants", Proc. Natl. Acad. Sci. USA, 84, pp. 4300-4304 (1988).

Ecker and Davis, "Inhibition Of Gene Expression In Plant Cells By Expression Of Antisense RNA", Proc. Natl. Acad. Sci. USA, 83, pp. 5372-5376 (1986).

Feth et al., "Determination Of Putrescine N-Methyltransferase By High-Performance Liquid Chromatography", Phytochemistry, 24, pp. 921-923 (1985).

Feth et al., "Regulation In Tobacco Callus Of Enzyme Activities Of The Nicotine Pathway", Planta, 168, pp. 402-407 (1986).

Feth and Wagner, "Determination Of Ornithine, Putrescine, N-Methylputrescine And N-Methylpyroline Pools In Tobacco Tissue By High-Performance Liquid Chromatography", Physiologica Plantarum, 75, pp. 71-74 (1989).

Hashimoto et al., "Putrescine And Putrescine N-Methyltransferase In The Biosynthesis Of Tropane Alkaloids In Cultured Roots of *Hyoscyamus albus*. I Biochemical Studies", Planta, 178, pp. 123-130 (1989).

(List continued on next page.)

*Primary Examiner*—David M. Naff
*Assistant Examiner*—Michael V. Meller
*Attorney, Agent, or Firm*—Gary L. Creason

[57] ABSTRACT

There is provided highly purified tobacco putrescine N-methyltransferase, a process for its purification, and production of PMT DNA sequence. The purification process includes the step of applying a tobacco root extract to an anion exchange medium and specifically eluting putrescine N-methyltransferase with an elution buffer comprising putrescine.

1 Claim, 5 Drawing Sheets

OTHER PUBLICATIONS

Hashimoto et al., "Putrescine And Putrescine N-Methyltransferase In The Biosynthesis Of Tropane Alkaloids In Cultured Roots Of *Hyoscyamus albus*. II Incorporation Of Labeled Precursors", *Planta*, 178, pp. 131-137 (1989).

Hemenway et al., "Analysis Of The Mechanism Of Protection In Transgenic Plants Expressing The Potato Virus X Coat Protein Or Its Antisense RNA", *EMBO J.*, pp. 1273-1280.

Lichtenstein, "Anti-sense RNA As A Tool To Study Plant Gene Expression", *Nature*, 333, 801-02 (1988).

Mizusaki et al., "Phytochemical Studies On Tobacco Alkaloids XIV. The Occurrence And Properties Of Putrescine N-Methyltransferase In Tobacco Roots", *Plant & Cell Physiol.*, 12, pp. 633-640 (1971).

Mizusaki et al., "Changes In The Activities Of Ornithine Decarboxylase, Putrescine N-Methyltransferase And N-Methylputrescine Oxidase In Tobacco Roots In Relation To Nicotine Biosynthesis", *Plant and Cell Physiol.*, 14, pp. 103-110 (1973).

Ohta and Yatazawa, "Metabolic Key Step Discriminating Nicotine Producing Tobacco Callus Strain From Ineffective One", *Biochem. Physiol. Pflanzen*, 175, pp. 382-385 (1980).

Rezanian et al., "Anti-Sense RNA's Of Cucumber Mosaic Virus In Transgenic Plants Assessed For Control Of The Virus", *Plant Molecular Biology*, 11, pp. 463-471 (1988).

Rodermel et al., "Nuclear-Organelle Interactions: Nuclear Antisense Gene Inhibits Ribulose Bisphosphate Carboxylase Enzyme Levels In Transformed Tobacco Plants", *Cell* 55, pp. 673-681 (1988).

Rothstein et al., "Stable And Heritable Inhibition Of The Expression Of Nopaline Synthase In Tobacco Expressing Antisense RNA", *Proc. Natl. Sci. USA*, 84, pp. 8439-8443 (1987).

Sandler et al., "Inhibition Of Gene Expression In Transformed Plants By Antisense RNA", *Plant Molecular Biology*, 11, pp. 301-310 (1988).

Saunders and Bush, "Comparison Of Nicotine Biosynthetic Enzymes In Nicotine Level Genotypes Of Burley Tobacco", *Agronomy Abstracts*, p. 84 (1978).

Saunders and Bush, "Enzyme Activities In Nicotine Biosynthesis In *Nicotiana tabacum*", *Journal of Natural Products* 41, p. 646 (1978).

Saunders and Bush, "Nicotine Biosynthetic Enzyme Activities In *Nicotiana tabacum* L. Genotypes With Different Alkaloid Levels", *Plant Physiol.*, 64, pp. 236-240 (1979).

Sheehy et al., "Reduction Of Polygalacturonase Activity In Tomato Fruit By Antisense RNA", *Proc. Natl. Acad. Sci. USA*, 85, pp. 8805-8809 (1988).

Smith et al., "Antisense RNA Inhibition Of Polygalacturonase Gene Expression In Transgenic Tomatoes", *Nature*, 334, pp. 724-726 (1988).

van der Krol et al., "An Anti-Sense Chalcone Synthase Gene In Transgenic Plants Inhibits Flower Pigmentation", *Nature*, 333, pp. 866-869 (1988).

van der Krol et al., "Modulation Of Eukaryotic Gene Expression By Complementary RNA Or DNA Sequences", *Biotechniques*, 6, pp. 958-976 (1988).

van der Krol et al., "Antisense Genes In Plants; An Overview", *Gene*, 72, pp. 45-50 (1988).

Wagner et al., "The Regulation Of Enzyme Activities Of The Nicotine Pathway In Tobacco", *Physiol. Plantarum*, 68, pp. 667-672 (1986).

Wagner et al., "Regulation In Tobacco Callus Of Enzyme Activities Of The Nicotine Pathway", *Planta*, 168, pp. 408-412 (1986).

METHOD OF PURIFYING PUTRESCINE N-METHYLTRANSFERASE FROM TOBACCO PLANT EXTRACT WITH A POLYAMINE

TECHNICAL FIELD OF THE INVENTION

The present invention relates to highly purified putrescine N-methyltransferase, to a novel process for its purification, and to its antisense and sense genes. In particular, this invention relates to the use of the sense and antisense putrescine N-methyltransferase genes to create transgenic tobacco plants having genetically altered nicotine levels. Such transgenic plants are useful in the production of cured tobacco for use in the tobacco industry.

BACKGROUND OF THE INVENTION

Various processes have been employed for the removal of nicotine from tobacco. Most of those processes, however, are not sufficiently selective for nicotine. They remove other ingredients from the tobacco, thereby adversely affecting its flavor and aroma. In addition, such processes are typically complex and expensive.

Nicotine, and biologically synthesized compounds in general, are formed through sequences of biochemical reactions, wherein each reaction is catalyzed by a different enzyme. The particular reaction sequence leading to a given compound is known as a pathway. One approach for inhibiting the operation of a pathway, and thus output of its end product, is reducing the amount of a required enzyme in the pathway. If the enzyme's abundance, relative to the other enzymes of the pathway, is normally low enough to make that enzyme rate-limiting in the pathway's operation, then any reduction in the enzyme's abundance will be reflected in lowered production of the end product. If the enzyme's relative abundance is not normally rate limiting, its abundance in the cell would have to be reduced sufficiently to make it rate-limiting, in order for the pathway's output to be diminished. Similarly, if the enzyme's relative abundance is rate limiting, then any increase in its abundance will result in increased production of the pathway's end product.

Nicotine is formed primarily in the roots of the tobacco plant and subsequently is transported to the leaves, where it is stored (Tso, *Physiology and Biochemistry of Tobacco Plants*, pp. 233-34, Dowden, Hutchinson & Ross, Stroudsburg, PA (1972)). The nicotine molecule is comprised of two heterocyclic rings, a pyridine moiety and a pyrrolidine moiety, each of which is derived from a separate biochemical pathway. The pyridine moiety of nicotine is derived from nicotinic acid. The pyrrolidine moiety of nicotine is provided through a pathway leading from putrescine to N-methylputrescine and then to N-methylpyrroline. An obligatory step in nicotine biosynthesis is the formation of N-methylputrescine from putrescine (Goodwin and Mercer, *Introduction to Plant Biochemistry*, pp. 488-91, Pergamon Press, New York, (1983)).

Conversion of putrescine to N-methylputrescine is catalyzed by the enzyme putrescine N-methyltransferase ("PMT"), with S-adenosylmethionine serving as the methyl group donor. PMT appears to be the rate-limiting enzyme in the pathway supplying N-methylpyrroline for nicotine synthesis in tobacco (Feth et al., "Regulation in Tobacco Callus of Enzyme Activities of the Nicotine Pathway", *Planta*, 168, pp. 402-07 (1986); Wagner et al., "The Regulation of Enzyme Activities of the Nicotine Pathway in Tobacco", *Physiol. Plant.*, 68, pp. 667-72 (1986)).

A relatively crude preparation of PMT (30-fold purification) has been subjected to limited characterization (Mizusaki et al., "Phytochemical Studies on Tobacco Alkaloids XIV. The Occurrence and Properties of Putrescine N-Methyltransferase in Tobacco Plants", *Plant Cell Physiol.*, 12, pp. 633-40 (1971)). The purification steps leading to that preparation were limited to ammonium sulfate precipitation from the initial extract and gel filtration chromatography. Id.

Antisense RNA technology allows the production of plants characterized by levels of an enzyme (or other protein) that are significantly lower than those normally contained by the plants. Ordinarily, transcription of a gene coding for a target enzyme gives rise to a single-stranded mRNA, which is then translated by ribosomes to yield the target enzyme. An antisense RNA molecule is one whose nucleotide sequence is complementary to some portion of the target mRNA molecule. The antisense RNA molecule, thus, will undergo complementary base pairing (hybridization) with the target mRNA molecule, rendering the target mRNA molecule unavailable for translation, more susceptible to degradation, or both. The ability of the cell to produce the specific enzyme coded for by the target mRNA is thus inhibited.

Antisense technology has been employed in several laboratories to create transgenic plants characterized by lower than normal amounts of specific enzymes. For example, plants with lowered levels of chalcone synthase, an enzyme of a flower pigment biosynthetic pathway, have been produced by inserting a chalcone synthase antisense gene into the genome of tobacco and petunia. These transgenic tobacco and petunia plants produce flowers with lighter than normal coloration (Van der Krol et al., "An Anti-Sense Chalcone Synthase Gene in Transgenic Plants Inhibits Flower Pigmentation", *Nature*, 333, pp. 866-69 (1988)). Antisense RNA technology has also been successfully employed to inhibit production of the enzyme polygalacturonase in tomatoes (Smith et al., "Antisense RNA Inhibition of Polygalacturonase Gene Expression in Transgenic Tomatoes", *Nature*, 334, pp. 724-26 (1988); Sheehy et al., "Reduction of Polygalacturonase Activity in Tomato Fruit by Antisense RNA", *Proc. Natl. Acad. Sci. USA*, 85, pp. 8805-09 (1988)), and the small subunit of the enzyme ribulose bisphosphate carboxylase in tobacco (Rodermel et al., "Nuclear-Organelle Interactions: Nuclear Antisense Gene Inhibits Ribulose Bisphosphate Carboxylase Enzyme Levels in Transformed Tobacco Plants", *Cell*, 55, pp. 673-81 (1988)). Alternatively, transgenic plants characterized by greater than normal amounts of a given enzyme may be created by transforming the plants with the gene for that enzyme in the sense (i.e., normal) orientation.

Genetic engineering of tobacco plants to lower or raise levels of nicotine through altered levels of PMT has not been possible, because a method for cloning PMT genes without prior purification of the PMT enzyme is not known, and a method for purification of the PMT enzyme was not known prior to this invention.

SUMMARY OF THE INVENTION

Figure 1:
FIG. 1 is a reproduction of a photograph of a 12.5%, silver-stained, SDS-polyacrylamide gel showing the pattern of proteins obtained at successive stages of the tobacco PMT purification process. Lanes 1 and 6: molecular weight standard proteins (phosphorylase B, 95.5 kD; glutamate dehydrogenase, 55.0 kD; ovalbumin, 43.0 kD; lactate dehydrogenase, 36.0 kD, carbonic anhydrase, 29.0 kD; lactoglobulin, 18.4 kD; cytochrome C, 12.4 kD). Lane 2: 40-65% ammonium sulfate fraction. Lane 3: PMT activity peak fraction from hydrophobic interaction column. Lane 4: concentrated putrescine-eluted material from anion exchange column. Lane 5: PMT activity peak fraction from free-flow isoelectric focussing of concentrated material from anion exchange column.

The present invention provides, for the first time, highly purified putrescine N-methyltransferase ("PMT"), and a novel process for its purification.

The purification process of this invention comprises the step of applying a tobacco plant extract to an anion exchange medium, wherein the application temperature and the pH and composition of the extract are such that PMT is retained by the anion exchange medium. The PMT is then eluted from the anion exchange medium with an elution buffer comprising an effective amount of a polyamine, wherein the elution temperature and the pH and chemical composition of the elution buffer are such that but for the polyamine, the PMT would be retained by the anion exchange medium.

In a preferred embodiment, the eluate of the anion exchange medium is concentrated by directly applying the eluate to a chromatography medium having an affinity for PMT in the presence of the anion exchange medium elution buffer, and then eluting the bound material. Most preferably, the outlet from the anion exchange column is connected to the inlet of an omega-aminohexyl agarose column, on which dilute PMT from the anion exchange column is collected, for subsequent elution in a more concentrated form.

The PMT of this invention has a molecular weight of between about 55 and 65 kilodaltons, a native isoelectric point of between about pH 5.0 and 6.0, a $K_m$ for putrescine of between about 300 $\mu M$ and 500 $\mu M$, and a $K_m$ for S-adenosylmethionine of between about 100 $\mu M$ and 150 $\mu M$. In a preferred embodiment, the PMT comprises a sequence of 17 amino acids selected from the amino acid sequences defined in the Sequence Listing as SEQ ID NO:1, SEQ ID NO:2, and SEQ ID NO:3.

The present invention also provides sense and antisense recombinant DNA molecules encoding putrescine N-methyltransferase, and vectors comprising those recombinant DNA molecules, as well as transgenic tobacco cells and plants transformed with those DNA molecules and vectors. The transgenic tobacco cells and plants of this invention are characterized by lower or higher nicotine content than untransformed control tobacco cells and plants.

DETAILED DESCRIPTION OF THE INVENTION

Purification Of PMT

Starting material for purification of PMT consists of tobacco roots. Preferably, the roots are harvested from hydroponically grown tobacco plants. Hydroponic cultivation facilitates growth of the plants under highly controlled, reproducible conditions, and it allows efficient harvest of the extensive, filamentous root system in a clean, intact condition.

Tobacco seeds are allowed to germinate at or near the surface of a moist plant potting mixture. Most preferred conditions are about 80° F. and 60% relative humidity. About two weeks after seed germination, seedlings are thinned (removed) to leave sufficient room for unhindered growth of the remaining seedlings to a stage at which they are about six inches tall, and have about six leaves. When the seedlings reach a height of about six inches they are typically transplanted, with root system and pellet of potting material intact, into a hydroponic device containing a suitable nutrient solution and a means for aeration (oxygenation) of the nutrient solution. The hydroponic device also should provide for replenishment of the dissolved nutrients, and should be of a size sufficient to accommodate a fully grown tobacco plant.

It is well known in the art that removal of the flower head (topping), a standard practice in commercial tobacco cultivation, increases root growth and increases nicotine content of the leaves. Therefore, plants to be used as a starting material for purification of PMT normally are topped at an appropriate stage of development. The appropriate interval separating planting and topping depends on several factors including, inter alia, plant variety, light intensity, photoperiod, soil and air temperatures, soil moisture, and mineral nutrition. Typically, however, the roots are harvested 3 to 7 days after topping. The optimal time for topping a given tobacco variety cultivated under a given set of growing conditions can readily be determined by one of ordinary skill in the art.

Preferably, the harvested roots are washed with cold water, and then residual water is removed by aspiration in a Buchner funnel. The washed roots are then either used fresh, or frozen at −80° C. immediately after harvesting. The frozen roots are stored at about −80° C. until use.

For a typical PMT purification procedure, between about 400 and 600 g of frozen root tissue per liter of extraction buffer is homogenized in a high speed blender. The extraction buffer typically contains effective amounts of one or more buffering agents, one or more reducing agents, one or more heavy metal chelating agents, one or more water activity modifying agents, and one or more protease inhibitors. Preferably, the extraction buffer also will contain an effective amount of one or more phenolic compound adsorbing agents. The effective amounts of these agents depends on the particular agents used; however, amounts used generally will be chosen from among the typical amounts used during purification of plant proteins. The choice of agents and their effective amounts is, thus, well within the skill of the ordinary worker.

The pH of the extraction buffer should be between about 7.2 and 8.3, and preferably about 7.5. Any water-soluble compound that has a dissociation constant ($pK_a$) giving it effective pH buffering capacity at the desired pH may be used. Preferred buffering agents are also essentially transparent to ultraviolet light. Suitable buffering agents include, inter alia, tris(hydroxymethyl)aminomethane ("Tris"), imidazole, phosphate, N-morpholinopropane sulfonic acid ("MOPS"), N-tris(hydroxymethyl)methyl-2-aminoethane sulfonic acid ("TES"), triethanolamine, and N-tris(hydroxymethyl)-methyl-glycine ("Tricine"). Tris buffer is preferred.

Reducing agents are added to the extraction buffer in order to inhibit possible oxidation of protein sulfhydryl groups, and possible oxidation of plant phenolic compounds to reactive free radicals, both of which events might inactivate PMT. Suitable reducing agents include, inter alia, dithiothreitol ("DTT"), dithioerythritol, 2-mercaptoethanol, thioglycolate, glutathione, cysteine, and ascorbate. DTT and ascorbate are preferred.

Heavy metal chelating agents are added to the extraction buffer in order to prevent activation of proteases and possible inactivation of PMT by heavy metals through direct interaction with PMT or through promotion by the metals of oxidation of phenolics to species that inactivate PMT. The preferred heavy metal chelating agent is ethylene diaminetetraacetic acid ("EDTA"), but other conventional chelating agents, such as ethylene glycol bis(beta-aminoethyl ether) N,N,N',N'-tetraacetic acid ("EGTA") and citrate, may be used.

Water activity modifying agents are added to the extraction buffer in order to stabilize PMT against possible denaturation and other more subtle conformational changes that might result in PMT inactivation. Such water activity modifying agents are non-ionic, hydrophilic compounds that lower the water activity of an aqueous solution to which they are added. Glycerol, ethylene glycol, and low molecular weight polyethyleneglycol (e.g., "PEG 400") are preferred, but glucose, sucrose, fructose, and sorbitol are examples of other compounds useful as water activity modifying agents.

Protease inhibitors usually are added to the extraction buffer in order to prevent possible inactivation of PMT through proteolytic cleavage by proteolytic enzymes that may be released during tissue homogenization. Useful protease inhibitors include, inter alia, phenylmethylsulfonyl fluoride ("PMSF"), leupeptin, aprotinin, chymostatin and pepstatin. PMSF and leupeptin are preferred.

A phenolic compound adsorbing agent preferably is added to the extraction buffer to remove phenolic plant compounds that might, if present, inactivate or precipitate PMT following their oxidation when the plant cells are broken. Typically, insoluble polyvinylpyrrolidone ("PVPP") and Amberlite XAD-4 are suspended in the extraction buffer to adsorb phenolic compounds. Other materials that remove or inactivate phenolic compounds without significant harm to PMT enzyme activity could be included with or substituted for PVPP or Amberlite XAD-4.

Prior to addition of the root tissue, the extraction buffer is cooled to between about −15° and −20° C. to form a frozen slurry. During the homogenization process, the temperature of the homogenate should not be allowed to rise above about 3° to 5° C.

As will be appreciated by those of ordinary skill in the art, the quantity of root tissue used in the process can be varied, but the approximate weight of the tissue used should be measured, and the amounts of other components used adjusted accordingly.

After homogenization, insoluble material (including PVPP with adsorbed phenolics) preferably is removed from the homogenate. Preferably, this is accomplished by sedimentation for between about 30 to 90 minutes at about 4° C., in a refrigerated centrifuge set at about 10,000 to 20,000× g. The soluble extract (i.e., the supernatant) is decanted after sedimentation of the insoluble material. The final protein concentration of the soluble extract is generally about 2.5 to 3.5 mg/ml.

The soluble extract is subjected to ammonium sulfate fractionation, and a 40% to 65% ammonium sulfate fraction (precipitate) is collected from the soluble extract according to standard methods (Scopes, *Protein Purification Principles and Practice.* pp. 48–52, Springer-Verlag, New York (1982)). That fraction then is dissolved in about 0.1 to 0.4 ml of a dissolution buffer per g of root weight.

The preferred buffer for dissolution of the 40% to 65% ammonium sulfate fraction contains effective amounts of a buffering agent, a heavy metal chelating agent, a reducing agent, a water activity-modifying agent, and protease inhibitors. The most preferred dissolution buffer contains Tris buffer (pH about 7.5) (about 10 to 20 mM), EDTA (about 1 to 10 mM), glycerol (about 10 to 30%), DTT (about 1 to 10 mM), PMSF (about 0.2 to 10.0 mg/l), and leupeptin (about 0.2 to 10.0 mg/l). These buffer components are included for the purposes described above for the analogous components in the extraction buffer. The skilled worker will appreciate that these components may be substituted with others of similar function.

The ammonium sulfate fraction may then be desalted by standard techniques—e.g., dialysis or sieving chromatography—and the desalted fraction directly subjected to anion exchange chromatography, as described below. In a preferred embodiment, however, the ammonium sulfate fraction first is subjected to hydrophobic interaction chromatography.

Before the dissolved ammonium sulfate fraction is subjected to hydrophobic interaction chromatography, salt is added to give a salt concentration that is high enough to ensure that PMT binds to the hydrophobic interaction medium. The preferred concentration of added salt is 1.5 N. The preferred added salt is NaCl. Another useful salt is ammonium sulfate.

The preferred hydrophobic interaction medium comprises approximately spherical particles of cross-linked agarose gel, of a size suitable for chromatography, bearing covalently bonded phenyl groups. Such phenylagarose is commercially available as "phenyl-Sepharose CL-4B" (Pharmacia-LKB, Inc., Piscataway, NJ, Cat. No. 17-0810-14 01).

Hydrated phenylagarose is packed into a suitable chromatography column using standard procedures, and is equilibrated at about 4° to 8° C. with a high salt equilibration buffer having a pH of from between about 7.2 to 8.3, and preferably about 7.5. The preferred high salt equilibration buffer contains effective amounts of a buffering agent, a heavy metal chelating agent, a water activity modifying agent, a reducing agent, and salt at a concentration of between about 1.5 to 2.0 M. The most preferred high salt equilibration buffer solution contains about 10 mM Tris (pH about 7.5), about 1.5 M NaCl, about 1 mM EDTA, about 2 mM DTT, and about 20% (v/v) glycerol.

A sample of the salt-adjusted soluble extract (about 0.5 to 2.0 ml of extract per ml phenylagarose packed bed volume) is loaded onto the equilibrated phenylagarose column, and the column is washed with the equilibration buffer until the eluate becomes essentially free of proteinaceous material. If the buffering agent is transparent to ultraviolet light, this may be determined by measuring ultraviolet light absorbance at around 280 nm. Generally, the phenylagarose column is washed with about 5 to 7 column volumes of equilibration buffer. PMT remains bound to the hydrophobic interaction medium.

Proteins still adsorbed to the phenylagarose matrix (including PMT) are then eluted at 4° to 8° C. with between about 4 to 6 column volumes of an elution buffer containing a linear salt gradient decreasing from the load salt concentration (preferably about 1.5 M) to about 0.0 M, followed by an additional 2 to 3 column volumes of elution buffer without salt. Preferably, the elution buffer will include Tris (about 10 mM) (pH about 7.5), DTT (about 2 mM), and EDTA (about 1 mM), and glycerol (about 20% v/v).

Fractions of between about 0.01 to 0.03 column volumes are collected and assayed for PMT activity as described below and for absorbance at 280 nm. Typically, the pooled eluate fractions have a volume of between about 1 to 2 column volumes, and a protein concentration of between about 0.4 and 2.5 mg/ml.

It will be understood that salts other than the preferred NaCl may be used in the foregoing buffers. Such salts include potassium chloride and ammonium sulfate.

The critical step of the purification process of this invention is a novel anion exchange chromatography step, performed as described below. In order to perform this step, however, the tobacco plant extract applied to the column (e.g., preferably, the phenylagarose eluate) must have a pH and chemical composition such that the PMT in the extract will bind to the anion exchange medium. That is, the extract should have a pH of between about 7.2 and 8.3, comprise between about 0.0 and 10 mM salt, and preferably should further comprise the following: between about 5 and 15 mM of a buffering agent, between about 1 and 10 mM of a reducing agent, between about 10 and 30% (v/v) of a water activity modifying agent, and between about 1 and 5 mM of a heavy metal chelating agent. Most preferably, the tobacco plant extract comprises 10 mM Tris/HCl, pH 7.5, 2 mM DTT, 1 mM EDTA and 20% (v/v) glycerol.

The skilled worker will, of course, appreciate that the pH and salt concentration of the tobacco plant extract may be varied in concert from the values recited above, resulting in a load condition at which the PMT still will bind to the anion exchange medium. In particular, it is well known that an increase in salt concentration generally will decrease the binding of a protein to an anion exchange medium and an increase in pH generally will increase binding of a protein to an anion exchange medium. The skilled worker, therefore, could easily determine various combinations of salt concentration and pH, other than those recited above, at which PMT will bind to the anion exchange medium. The only constraint on the possible pH/salt concentration combinations is that the pH may not be so high as to denature and inactivate PMT. Generally, PMT should not be exposed for significant periods of time to a pH above about 9.

From the foregoing, it is clear that if the tobacco root extract to be applied to the anion exchange medium is an ammonium sulfate fraction or the eluate from the above-described hydrophobic interaction chromatography step, then it must be desalted into an appropriate buffer. This may be accomplished by any standard technique. For example, gel filtration chromatography (using, e.g., Sephadex G-25) or dialysis may be employed, using well known procedures. Preferably, such desalting will be accomplished by dialysis.

In a preferred process, the pooled eluate from the above hydrophobic interaction chromatography step (or another high salt tobacco root extract) is dialyzed at about 4° to 8° C. against a dialysis buffer with about 15 to 25 ml dialysis buffer per ml of pooled eluate or extract, for about 8 to 20 hours. Preferably, the dialysis buffer will be stirred. A dialysis membrane having a 10,000 kD cut-off is preferred. The chemical composition and pH of the dialysis buffer is chosen so that PMT in the dialyzed fraction will be retained by the anion exchange medium, as described above.

The anion exchange medium should consist of relatively rigid particles (e.g., crosslinked agarose), of a size suitable for chromatography, that bear one or more functional anion exchange moieties. Such anion exchange moieties may be selected, inter alia, from the group consisting of diethylaminoethyl, polyethyleneimino, tertiary amino, quaternary amino, p-aminobenzyl, and diethyl-(2-hydroxypropyl)aminoethyl. Such media are commercially available. An anion exchange medium bearing diethylaminoethyl ("DEAE") moieties is preferred. DEAE-agarose ("DEAE-Sepharose, Fast Flow", Pharmacia-LKB, Inc., Piscataway, NJ, Cat. No. 17-0709-01) is most preferred.

The anion exchange medium is equilibrated to the pH and salt condition of the equilibration buffer, according to standard procedures.

The equilibrated anion exchange medium then is packed according to standard procedures into a column (i.e., a hollow tube) having at its bottom a means of retaining the medium (e.g., a sintered glass disk) and an outlet tube. The top of the column is then covered and connected to an inlet tube. Then, preferably, equilibration buffer should be run through the column, and the pH and conductivity of the flowthrough monitored, to ensure that the medium is properly equilibrated.

The column should contain enough anion exchange medium so that the proteins in the tobacco plant extract to be applied would occupy no more than about 50% of the medium's capacity if they all were to bind. For example, when the tobacco plant extract to be applied is the above-described dialyzed phenylagarose eluate, the column should contain about 0.04 to 0.10 ml (packed bed volume) of DEAE-agarose per ml of dialyzed phenylagarose eluate.

Preferably, the column is packed and the medium equilibrated at the same temperature at which the tobacco plant extract is to be applied. If the column is to be washed or eluted at a warmer temperature than that at which the tobacco plant extract is applied, then the slurry containing the anion exchange matrix may be degassed prior to packing the column.

As described above for the tobacco plant extract to be applied to the anion exchange medium, the anion exchange medium equilibration buffer must have a pH and chemical composition such that PMT is retained by the medium. Similarly, the skilled worker easily may determine suitable pH/chemical composition combinations. The preferred equilibration buffer contains essentially no added salt and has a pH of between about 7.2 to 8.3, most preferably 7.5. A more preferred equilibration buffer contains effective amounts of a buffering agent, a heavy metal chelating agent, a reducing agent, and a water activity modifying agent. The most preferred equilibration buffer contains 10 mM Tris/HCl (pH 7.5), 1 mM EDTA, 2 mM DTT, and 20% (v/v) glycerol.

Preferably, the tobacco plant extract, the equilibration buffer and the anion exchange medium are all at a temperature of between about 2° to 10° C., and most preferably between about 4° to 8° C. before and during equilibration, loading, and washing of the column.

The tobacco plant extract is applied at a flow rate of between about 0.1 to 0.3 column volumes/min. The flowthrough from the tobacco plant extract application contains practically no PMT, and is discarded. The column is then washed with equilibration buffer until elution of proteinaceous material stabilizes at a low level. If the equilibration buffer does not contain a buffering agent that absorbs at 280 nm, the column is washed with elution buffer until the UV absorbance at 280 nm stabilizes at a low level. Typically, the anion exchange medium is washed with 5 to 12 column volumes of equilibration buffer with 10 mM NaCl, and then another 3 to 10 column volumes of equilibration buffer without NaCl. PMT is retained by the anion exchange medium during the washing step.

After washing, PMT is eluted from the anion exchange medium with an elution buffer comprising an effective amount of a polyamine, wherein the elution temperature and the pH and chemical composition of the elution buffer are such that but for the polyamine, the PMT would be retained by the anion exchange medium.

The polyamine in the elution buffer is selected from the group consisting of putrescine, N-methylputrescine, spermine, spermidine, agmatine, cadaverine, and mixtures thereof. Putrescine is the preferred polyamine. The polyamine should be present in the elution buffer at a concentration of between about 0.5 to 50 mM, preferably 1 to 10 mM, and most preferably at about 5 mM.

The elution buffer preferably further comprises effective amounts of a buffering agent, a heavy metal chelating agent, a reducing agent, and a water activity modifying agent. Those components are as described above for the extraction buffer. The effective amounts of these components may be determined without undue experimentation by the skilled worker. The pH of the elution buffer should be between about 7.2 and 8.3, preferably about 7.5. The anion exchange medium equilibration buffer, when supplemented with a polyamine, is a suitable elution buffer. A preferred elution buffer contains 10 mM Tris/HCl (pH 7.5), 1 mM EDTA, 20% (by volume) glycerol, 2 mM DTT, and 5 mM putrescine (1,4-diaminobutane) (Sigma Chemical Co., St. Louis, MO, Cat. No. P7505).

Elution of PMT from the anion exchange column is preferably carried out at between about 18° to 26° C. (i.e., room temperature). The elution buffer and the anion exchange column should be at the chosen elution temperature before elution is commenced.

To elute PMT from the column, elution buffer is applied at a flow rate of between about 0.02 to 0.10 column volumes/min, and fractions are collected from the bottom of the column. The eluate also may be collected into a single eluate pool. In the most preferred elution process, approximately one column volume of elution buffer is applied to the column, and the flow is then stopped. The anion exchange medium is left in contact with that aliquot of elution buffer for between about 1 to 6 hours, preferably about one hour. Application of elution buffer is then recommenced.

PMT elutes from the anion exchange medium very gradually. Typically, the anion exchange medium is eluted with between about 40 and 70 column volumes of elution buffer, and most preferably at least 50 column volumes of elution buffer. PMT activity of eluted fractions is assayed, as described below, to monitor PMT elution.

As PMT is recovered in a relatively dilute form and in a relatively large volume, it is desirable to concentrate the anion exchange eluate. The eluate may, for example, be applied to any chromatography medium which has an affinity for PMT in the presence of the anion exchange medium elution buffer, and from which the bound material can be eluted with good yield in a relatively concentrated form. Alternatively, the PMT may be precipitated. In a preferred process of this invention, the outlet from the anion exchange column, during elution, is connected to the inlet of the concentration column. In this way, the eluted PMT runs out of the anion exchange column and directly onto the concentration column, where it is adsorbed. After elution of PMT from the anion exchange column is complete, the outlet of that column is disconnected from the concentration column, and the PMT is eluted from the concentration column.

The preferred concentration column utilizes omega-aminohexyl agarose ("omega-aminohexyl-Sepharose 4B", Sigma Chemical Co., St. Louis, MO, Cat. No. A8894) ("AHS"), with a bed volume 10 to 30% that of the anion exchange column. The PMT is eluted from this column with an elution buffer comprising a relatively high concentration of salt, preferably 1.5 M NaCl. Preferably, the elution buffer further comprises effective amounts of a buffering agent, a heavy metal chelating agent, a reducing agent, and a water activity modifying agent. The most preferred elution buffer comprises 1.5 M NaCl, 10 mM Tris/HCl (pH 7.5), 1 mM EDTA, 20% (v/v) glycerol, and 2 mM DTT. The concentration column is preferably loaded and eluted at 4°–8° C.

The first 4 to 8 column volumes of eluate from the concentration column contains the majority of the PMT activity. This fraction is further concentrated, preferably in an ultrafiltration device (such as the "Centricon 30", available from Amicon Corp., Danvers, MA). After ultrafiltration the sample typically has a protein concentration of between about 0.04 and 0.70 mg/ml. Typically the PMT-containing fractions from several such concentration columns are pooled and further concentrated.

The PMT obtained after the anion exchange and sample concentration steps is further purified by preparative scale isoelectric focussing. Isoelectric focussing involves placing the sample mixture in a stabilized pH gradient, across which a voltage is then applied. Each protein species migrates electrophoretically toward the point in the pH gradient at which the net electrical charge of that protein species is zero. The pH at which a protein has a net electric charge of zero is called that protein's isoelectric point.

Various pH gradient stabilizing media, including, inter alia, sucrose solutions and polyacrylamide gels, can be used. Similarly, various methods of fractionating the pH gradient to recover proteins after isoelectric focussing can be employed. The pH gradient fractionation method should be chosen so as to be compatible with the gradient stabilizing medium.

The preferred pH gradient stabilizing medium is a sucrose solution (density gradient) contained in a glass tube. Most preferably, the sucrose density gradient contains a pH gradient ranging from about pH 5 to about pH 6. The preferred gradient fractionation method is precisely controlled liquid flow through a stopcock. Fractions collected are tested for pH and PMT activity. Apparatuses, chemicals, and protocols for isoelectric focussing are available from several commercial sources.

PMT isolated by the process of this invention is substantially free of other tobacco proteins, in that PMT is the predominant protein in the preparation. The few contaminating tobacco proteins in the preparation are separated from PMT by sodium dodecyl sulfate polyacrylamide gel electrophoresis ("SDS-PAGE"), according to standard techniques. In this way, sufficiently pure PMT for amino acid sequence analysis is obtained.

Characterization of PMT

Tobacco PMT is characterized by a molecular weight of between about 55 and 65 kilodaltons, as determined by SDS-PAGE, and a native isoelectric point of between about pH 5.0 and 6.0, as measured by isoelectric focussing.

Tobacco PMT is further characterized by the ability to catalyze the transfer of the methyl group of S-adenosylmethionine to the delta amino group of putrescine, and by high substrate specificity for putrescine.

The Michaelis-Menten constant ($K_m$) is defined as the substrate concentration at which the initial reaction velocity is equal to one half of the maximal velocity of the reaction. $K_m$ values vary widely, even for separate enzyme species that catalyze the same reaction. $K_m$ measurements are thus useful "identity markers" for enzymes. Partially purified tobacco PMT is characterized by a $K_m$ for putrescine of between about 300 and 500 $\mu$M. Highly purified tobacco PMT of the present invention is characterized by a $K_m$ for S-adenosylmethionine of between about 100 and 150 $\mu$M.

Determination of Partial Amino Acid Sequence of PMT

In preparation for amino acid sequence analysis, the standard technique of SDS-PAGE is used to separate PMT from the few contaminating proteins that remain after the anion exchange, sample concentration, and isoelectric focussing steps. Detailed protocols for SDS-PAGE are found in Laemmli, "Cleavage of Structural Proteins During the Assembly of the Head of Bacteriophage T4", *Nature*, 227, pp. 680–85 (1970); and in manuals supplied by manufacturers of electrophoresis equipment. By well known techniques, bands containing individual proteins are transferred electrophoretically (electroblotted) onto thin sheets or membranes, where they are retained and visualized. In one well-known method, protein bands are electroblotted onto glass microfiber sheets coated with a hydrophobic polycation, such as poly(4-vinyl-N-methylpyridinium) iodide, and visualized by a non-anionic agent such as fluorescamine. Another method involves electroblotting of proteins onto polyvinylidene difluoride membranes ("Immobilon-P", Millipore, Bedford, MA) and visualization of bands by an anionic dye such as amido black (Bauw et al, "Alterations in the Phenotype of Plant Cells Studied by NH$_2$-Terminal Amino Acid Sequence Analysis of Proteins Electroblotted from Two-Dimensional Gel-Separated Total Extracts", *Proc. Nat. Acad. Sci. USA* 84, pp. 4806–10 (1987); *A Practical Guide to Protein and Peptide Purification for Microsequencing*, Paul T. Matsudaira (ed.), Academic Press, New York, (1989)).

The aforementioned techniques for transferring isolated proteins from electrophoretic gels and visualizing the transferred proteins are preferred. However, it will be appreciated by those skilled in the art that variations in materials and procedures used to prepare electrophoretically isolated proteins for sequence analysis are not excluded from the present invention.

The bands constituting purified PMT are identified by apparent molecular weight (i.e., about 60 kD). Following transfer of the protein bands from electrophoresis gel to membrane, and visualization of the transferred bands, the pieces of membrane bearing the individual bands of purified PMT are cut out precisely, so as to avoid contamination from any adjacent protein band.

The protein bands (isolated as described above) constituting purified tobacco PMT are subjected to amino terminal sequence analysis by standard automated methods. Tobacco PMT proteins comprise an amino acid sequence selected from SEQ ID NO:1, SEQ ID NO:2, and SEQ ID NO:3.

Figure 5:
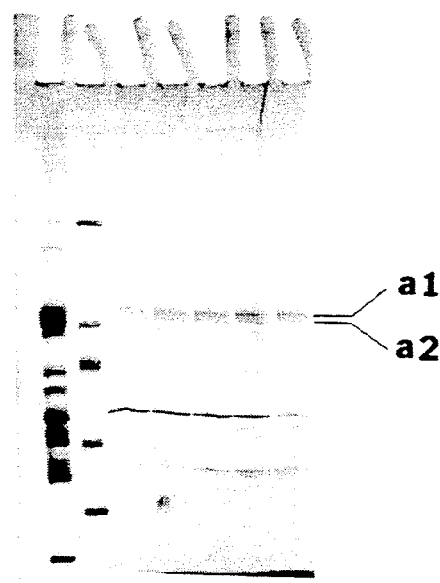
FIG. 5 is a reproduction of a photograph of a 12.5%, silver-stained, SDS-polyacrylamide gel showing the PMT protein bands ("a1" and "a2") that were cut out (after electroblotting onto an inert membrane) and subjected to amino acid sequence determination. Samples loaded onto the gel were aliquots from fractions from isoelectric focussing of putrescine-eluted material from an anion exchange column. The actual bands used for sequence analysis were from a separate (but similar) polyacrylamide gel that was loaded with aliquots of the same material analyzed on the gel in this figure.

SEQ ID NO:1 is from the "a1" band (FIG. 5). SEQ ID NO:2 is from the "a2" band (FIG. 5). SEQ ID NO:3 is the consensus sequence of SEQ ID NO:1 and SEQ ID NO:2.

Highly homologous sequences from closely adjacent purified protein bands suggest the existence of multiple forms of tobacco PMT protein. Such multiple forms of tobacco PMT protein may arise from post-translational modification of a single gene product, or from multiple forms of PMT genes.

Cloning Of PMT DNA Sequences

The partial amino acid sequences (SEQ ID NO:1, SEQ ID NO:2, SEQ ID NO:3) of the PMT proteins of this invention are used to design a set of oligonucleotides, one or more of which selectively hybridizes with PMT sequences in a tobacco root cDNA library. This selective hybridization is used to identify cDNA clones containing sequences encoding part or all of a PMT protein. A description of the design of oligonucleotide probes from amino acid sequences is presented in Chapter 11 of Sambrook et al. *Molecular Cloning—A Laboratory Manual,* Cold Spring Harbor Press (1989).

Synthesis of such oligonucleotide probes is carried out routinely with commercially available, automated equipment.

Construction of cDNA libraries is now a routine task in molecular biology laboratories. See generally Chapter 8 of Sambrook et al., supra. Similarly, screening of cDNA libraries with oligonucleotide probes, to identify clones containing sequences of interest, is now commonplace and well within the capability of those of skill in the art. A description of the use of oligonucleotides for screening cDNA libraries is found in Chapter 11 of the laboratory manual by Sambrook et al., supra. The cDNA clones selected on the basis of hybridization with oligonucleotide probes are characterized as to size, presence of restriction sites, and nucleotide sequence. Such methods of DNA analysis are well described in, inter alia, publications by Sambrook et al., supra, and Ausubel et al. *Short Protocols in Molecular Biology,* Green Publishing Associates and Wiley Interscience, New York (1989). Any PMT cDNA clone obtained in this way can itself be used as a probe for identification of additional PMT cDNA clones.

A tobacco (*Nicotiana tabacum* L. var. NK326) genomic library is commercially available (Clonetech Laboratories, Inc., Palo Alto, CA). Such a genomic library is screened according to protocols supplied by the vendor, to obtain the chromosomal gene(s) encoding tobacco PMT.

Accordingly, this invention provides recombinant DNA molecules encoding tobacco PMT proteins.

Production Of Transgenic Tobacco Cells and Plants Stably Transformed With PMT DNA Sequences In The Sense Or Antisense Orientation This invention also provides transgenic tobacco cells and plants stably transformed with recombinant DNA molecules, operably linked to regulatory sequences, that encode tobacco PMT proteins and that encode PMT antisense RNA molecules.

To produce a tobacco plant having lower nicotine content than an untransformed control tobacco plant, a tobacco cell is transformed with an artificial PMT antisense transcriptional unit comprising a partial PMT cDNA sequence, a full-length PMT cDNA sequence, a partial PMT chromosomal sequence, or a full-length PMT chromosomal sequence, cloned in the antisense orientation, with appropriate operably linked regulatory sequences. Appropriate regulatory sequences include a transcription initiation sequence ("promoter"), and a polyadenylation/transcription termination sequence.

Expression of antisense sequences in transgenic tobacco plants typically utilizes the Cauliflower Mosaic Virus (CaMV) 35S promoter. See, e.g., Cornelissen et al., "Both RNA Level and Translation Efficiency are Reduced by Anti-Sense RNA in Transgenic Tobacco", *Nucleic Acids Res.* 17, pp. 833–43 (1989); Rezaian et al., "Anti-Sense RNAs of Cucumber Mosaic Virus in Transgenic Plants Assessed for Control of the Virus", *Plant Molecular Biology* 11, pp. 463–71 (1988); Rodermel et al., "Nuclear-Organelle Interactions: Nuclear Antisense Gene Inhibits Ribulose Bisphosphate Carboxylase Enzyme Levels in Transformed Tobacco Plants", *Cell* 55, pp. 673–81 (1988); Smith et al., "Antisense RNA Inhibition of Polygalacturonase Gene Expression in Transgenic Tomatoes", *Nature* 334, pp. 724–26 (1988); Van der Krol et al., "An Anti-Sense Chalcone Synthase Gene in Transgenic Plants Inhibits Flower Pigmentation", *Nature* 333, pp. 866–69 (1988). Use of the CaMV 35S promoter for expression of PMT in the transformed tobacco cells and plants of this invention is preferred. Use of the CaMV promoter for expression of other recombinant genes in tobacco roots has been well described (Lam et al., "Site-Specific Mutations Alter In Vitro Factor Binding and Change Promoter Expression Pattern in Transgenic Plants", *Proc. Nat. Acad. Sci. USA* 86, pp. 7890–94 (1989); Poulsen et al. "Dissection of 5' Upstream Sequences for Selective Expression of the *Nicotiana plumbaginifolia* rbcS-8B Gene", *Mol. Gen. Genet.* 214, pp. 16–23 (1988)).

While use of the CaMV 35S promoter is preferred, it should be appreciated that other promoters are successfully used for expression of foreign genes in tobacco plants, and the use of promoters other than the CaMV 35S promoter falls within the scope of the present invention.

Various transcription termination sequences are known. The source and identity of the transcription termination sequence is primarily a matter of convenience. For example, the nopaline synthase ("NOS"), octopine synthase ("OCS"), and CaMV polyadenylation/transcription termination sequences are used for expression of foreign genes in transgenic tobacco plants, and would be useful for expression of PMT sequences. See, e.g., Rezian et al., supra. and Rodermel et al., supra.

Standard techniques, such as restriction mapping, Southern blot hybridization, and nucleotide sequence analysis, are then employed to identify clones bearing PMT sequences in the antisense orientation, operably linked to the regulatory sequences (i.e. promoter and polyadenylation/transcription termination sequences).

There is a well-developed technology applicable for introduction of exogenous DNA into the genome of tobacco cells so as to produce transgenic tobacco cells, stably transformed with the exogenous DNA. Any of the numerous known methods of tobacco cell transformation can be used in practicing the present invention. Methods for tobacco cell transformation are conveniently classified on the basis of whether or not they utilize components of the Agrobacterium system.

*Agrobacterium tumefasciens* is a gram negative bacterium that harbors a plasmid with nucleotide sequences called "T-DNA" (for transferred DNA), that are efficiently transferred and integrated into chromosomes of dicotyledonous plants (including tobacco) in nature, causing tumor growth on infected plants. This naturally-occurring vector system for integration of foreign DNA into plant chromosomes has been extensively studied, modified, and exploited for plant genetic engineering. (Deblaere et al. "Efficient Octopine Ti Plasmid-Derived Vectors for Agrobacterium-Mediated Gene Transfer to Plants", *Nucleic Acids Research* 13, pp.

4777-88 (1985)). Naked recombinant DNA molecules comprising PMT DNA sequences operably linked, in the sense or antisense orientation, to regulatory sequences are joined to appropriate T-DNA sequences by conventional methods. These are introduced into tobacco protoplasts by polyethylene glycol techniques or by electroporation techniques, both of which are standard. Alternatively, such vectors comprising recombinant DNA molecules encoding PMT are introduced into live Agrobacterium cells, which then transfer the DNA into the tobacco plant cells (Rogers et al., "Gene Transfer in Plants: Production of Transformed Plants Using Ti Plasmid Vectors" *Methods in Enzymology* 118, pp. 627-40 (1986)).

Although widely used in the art, Agrobacterium technology is not a necessary component of the present invention. Transformation by naked DNA without accompanying T-DNA vector sequences can be accomplished via fusion of tobacco protoplasts with DNA-containing liposomes or via electroporation. (Shillito et al., "Direct Gene Transfer to Protoplasts of Dicotyledonous and Monocotyledonous Plants by a Number of Methods, Including Electroporation", *Methods in Enzymology* 153, pp. 313-36 (1987)). Naked DNA unaccompanied by T-DNA vector sequences can also be used to transform tobacco cells via inert, high-velocity microprojectiles (BIOLISTIC TM Particle Delivery System, DuPont, Wilmington, DE).

Preferably, the PMT recombinant DNA molecules and vectors used to produce the transformed tobacco cells and plants of this invention will further comprise a dominant selectable marker gene. Suitable dominant selectable markers for use in tobacco include, inter alia, antibiotic resistance genes encoding neomycin phosphotransferase, hygromycin phosphotransferase, and chloramphenicol acetyltransferase. Another well-known dominant selectable marker suitable for use in tobacco is a mutant dihydrofolate reductase gene that encodes methotrexate-resistant dihydrofolate reductase (Deblaere et al., supra). DNA vectors containing suitable antibiotic resistance genes, and the corresponding antibiotics are commercially available.

Transformed tobacco cells are selected out of the surrounding population of non-transformed cells by placing the mixed population of cells into a culture medium containing an appropriate concentration of the antibiotic (or other compound normally toxic to tobacco cells) against which the chosen dominant selectable marker gene product confers resistance. Thus, only those tobacco cells that have been transformed will survive and multiply.

Transformed cells are induced to regenerate intact, fertile, tobacco plants through application of tobacco cell and tissue culture techniques that are well known in the art. The method of plant regeneration is chosen so as to be compatible with the method of transformation. Verification of the stable presence and the orientation of the PMT sequence in the genome of putatively transgenic tobacco plants is by Mendelian inheritance of the PMT sequence, as revealed by standard methods of DNA analysis applied to progeny resulting from controlled crosses.

After regeneration of transgenic tobacco plants from transformed cells, the introduced PMT sequence is readily transferred to other tobacco varieties through conventional plant breeding practices and without undue experimentation.

Decreased levels of nicotine in the PMT antisense transgenic tobacco plants are detected by standard nicotine assays.

Those familiar with the recombinant DNA methods described above will recognize that one could employ a full-length PMT cDNA molecule or a full-length PMT chromosomal gene, joined in the sense orientation, with appropriate operably linked regulatory sequences, to construct transgenic tobacco cells and plants. (Those of skill in the art will also recognize that appropriate regulatory sequences for expression of genes in the sense orientation include any one of the known eukaryotic translation start sequences, in addition to the promoter and polyadenylation/transcription termination sequences described above). Such transformed tobacco plants are characterized by increased levels of PMT protein, and thus by higher nicotine content than untransformed control tobacco plants.

It should be understood, therefore, that use of PMT DNA sequences to decrease or to increase levels of PMT protein, and thereby to decrease or increase the nicotine content in tobacco plants, falls within the scope of the present invention.

In order that this invention may be better understood, the following examples are set forth. These examples are for purposes of illustration only, and are not to be construed as limiting the scope of the invention in any matter.

EXAMPLES

Composition of Buffer Solutions

Buffer A
 50 mM Tris/HCl, pH 7.5
 5 mM EDTA (free acid)
 20% (v/v) glycerol
 2 mM DTT
 0.5% (w/v) sodium ascorbate
 2 % (w/v) PEG 400
 0.4 mg/l PMSF (from a 1 mg/ml stock solution)
 0.4 mg/l leupeptin (from a 1 mg/ml stock solution)
 100 g/l PVPP
 40 g/l Amberlite XAD-4
Buffer B
 10 mM Tris/HCl, pH 7.5
 1 mM EDTA (free acid)
 20% (v/v) glycerol
 2 mM DTT
 0.4 mg/l PMSF (from a 1 mg/ml stock solution)
 0.4 mg/l leupeptin (from a 1 mg/ml stock solution)
Buffer C
 10 mM Tris/HCl, pH 7.5
 1 mM EDTA (free acid)
 20% (v/v) glycerol
 2 mM DTT

Protease Inhibitor Stock Solutions

PMSF (1 mg/ml) was dissolved in dimethylformamide and stored in 2.1 ml aliquots at −20° C. until use.

Leupeptin (1 mg/ml) was dissolved in distilled water and stored in 2.1 ml aliquots at −20° C. until use.

Preparation of Crude Extract

Approximately one kg of roots from hydroponically grown tobacco (*Nicotiana tabacum* L. var. Burley 21) plants was harvested at 3 days after topping. The harvested roots were washed with cold water and placed on a Buchner funnel, where water was removed by aspiration. The washed roots were stored frozen at −80° C. The frozen roots were added to 2.5 liters of Buffer A that had been chilled into a frozen slurry, in a one-gallon Waring blender. The roots were mixed into the buffer slurry with a large spoon. The blender was started on a low speed setting, followed by additional homogenization at a medium speed setting. Care was taken to avoid permitting the temperature of the homogenate to rise above 3°-5° C.

The extract was dispensed into centrifuge bottles, and insoluble debris was pelleted by centrifugation at 13,680× g for 70 minutes at 4° C.

The supernatant was decanted, and its volume was 2.37 l. Approximately 0.77 g of DTT was added to the extract.

Ammonium Sulfate Fractionation

Crystalline ammonium sulfate was slowly added to the extract in the amount of 22.6 g per 100 ml of extract, so as to bring the extract to 40% of saturation with ammonium sulfate. The extract with ammonium sulfate was stirred for two hours at 4° C.

The 40% ammonium sulfate precipitate was removed by centrifugation at 27,500× g for 30 min at 4° C. An additional 0.33 g of DTT was added per liter of extract. Crystalline ammonium sulfate, in the amount of 15.3 g per 100 ml of extract, was slowly added to the extract, so as to increase the ammonium sulfate concentration from 40% to 65% saturation. The extract with 65% ammonium sulfate was stirred overnight at 4° C. The 40-65% ammonium sulfate fraction was pelleted by centrifugation at 27,500× g for 70 minutes at 4° C., and the supernatant was discarded.

The 40-65% ammonium sulfate precipitate was dissolved in Buffer B to yield a total volume of 200 ml, and then 17.53 g of NaCl was added and allowed to dissolve during stirring on ice. The dissolved 40-65% fraction with added NaCl was centrifuged at 47,800× g for 30 min at 4° C., and the pellets were discarded.

Preparation of a crude extract and ammonium sulfate fractionation were performed 3 more times, substantially as described above, and the 4 resulting 40-65% ammonium sulfate fractions (200 ml each) were pooled. The 800 ml pool thus formed represented a total of 5.239 kg of root tissue.

Hydrophobic Interaction Chromatography

A phenyl-Sepharose CL 4B (Pharmacia Inc., Piscataway, N.J., Cat. No. 17-0810-01) hydrophobic interaction column (5 cm ×20 cm) was equilibrated with Buffer C supplemented with 1.5 M NaCl. An 800 ml pool of 40-65% clarified ammonium sulfate fraction, representing 5.239 kg of root tissue, was then loaded onto the equilibrated phenyl-Sepharose column. The column was washed with Buffer C supplemented with 1.5 M NaCl until a stable baseline of 280 nm absorbance was obtained, indicating that practically all unbound protein had been removed. PMT was then eluted with a 2 l, linear gradient of NaCl decreasing from 1.5 M to 0.0 M in Buffer C. The column was further washed with an additional 1 l of Buffer C. Fractions of 12 ml each were collected, and fractions (every third fraction in and around the PMT activity peak, and every tenth fraction elsewhere in the gradient) were subsequently assayed for PMT activity as described below. The hydrophobic interaction chromatography was carried out at 4° C., with a flow rate of 4.7 ml/min.

Phenyl-Sepharose fractions #86 through #116, which contained PMT activity, were pooled and the pool was dialyzed for about 18 hours, against 9 l of Buffer C, with constant stirring. The dialyzed sample was separated into 4 aliquots of 100 ml each, and stored at −80° C.

Assay of PMT Activity

Each reaction tube contained the following:
12.5 μmol Tris/HCl pH 8.3
0.25 μmol EDTA
1.25 μmol 2-mercaptoethanol
0.9 μmol putrescine
0.15 μmol unlabelled S-adenosylmethionine
0.18 μmol [$^{14}$C-methyl]S-adenosylmethionine (57 nCi/nmol) enzyme sample Total Volume =0.25 ml The reaction was started by addition of the enzyme sample, and it was carried out at 30° C. for 30 minutes. The reaction was stopped by addition of 0.5 ml of 10% (w/v) NaOH saturated with NaCl.

The radioactive product, N-[$^{14}$C-methyl]putrescine, was separated from the substrate by solvent extraction into chloroform. After vortexing the stopped reaction mixture with 1 ml of chloroform for 90 seconds, the organic and aqueous phases were separated by centrifugation at 1600× $g_{av}$ for 5 minutes. A 0.5 ml aliquot of the organic phase was then assayed. The 0.5 ml aliquot of the organic phase was added to 9.5 ml of liquid scintillation cocktail (Beckman Instruments, Columbia, MD) and radioactivity was measured by standard procedures with a liquid scintillation counter.

One unit of PMT activity is defined as one nanomole of product formed per 30 min., at 30° C.

Negative controls were included with all PMT assays. Negative controls consisted of reaction mixtures minus enzyme, or reaction stopped with NaOH at time zero.

Anion Exchange Chromatograghy

Two 100 ml aliquots of the phenyl-Sepharose-purified sample were thawed and then loaded, at 4° C., at a flow rate of 1.5 ml/min, onto a DEAE-Sepharose "Fast Flow" (Pharmacia-LKB, Piscataway, NJ, Cat. No. 17-0709-01, Lot No. 0B-05854) column (1 cm ×14.5 cm) that had been equilibrated at 4° C. with Buffer C.

The DEAE-Sepharose column was then washed at a flow rate of 1.5 ml/min with 70 ml Buffer C containing 10 mM NaCl until a stable 280 nm baseline was obtained. The column was then re-equilibrated with 50 ml of Buffer C. without NaCl. The column was then raised to room temperature (24° C.), and the void volume of the column was replaced with Buffer C containing 5 mM putrescine (Sigma Chemical Co., St. Louis, MO, Cat. No. P7505, Lot No. 39F0039). The column was held at 24° C. with no flow for about 1 hour, and then PMT was eluted at 24° C. with 632 ml of Buffer C containing 5 mM putrescine, at a flow rate of 0.7 ml/min (15 hours).

PMT Concentration by Adsorption

The eluted PMT from the DEAE-Sepharose column was collected directly onto a column (1 cm ×3 cm) of omega-aminohexyl-Sepharose 4B ("AHS") (Sigma Chemical Co., St. Louis, MO, Cat. No. A8894) that was maintained at 4° C. PMT was eluted from the AHS column with Buffer C containing 1.5 M NaCl, at a flow rate of 1.6 ml/min. Four fractions of 12–15 ml each were collected and assayed for PMT activity as described above. The first fraction (14.7 ml) contained more than 80% of the total PMT activity recovered from the AHS concentration column.

Ultrafiltration

For further concentration, 13.7 ml of the first AHS fraction was divided into 6 aliquots and placed in "Centricon 30" (Amicon, Danvers, MA) ultrafiltration devices and concentrated about 25-fold. Concentrates from six such devices were pooled, diluted about 80-fold with Buffer C without added salt, and subjected to a second round of ultrafiltration in a single "Centricon 30," until the total volume was about 150 μl. The 150 μl of concentrate was stored at −80° C.

Preparative Isoelectric Focussing

PMT purified through the DEAE/AHS stage (including concentration by ultrafiltration) was further purified by isoelectric focussing. Preparative scale isoelectric focussing was performed with commercially available ampholytes (Pharmacia-LKB, Piscataway, NJ) in a sucrose density gradient (1.6 cm ×21 cm). The pH gradient was prepared according to the ampholyte vendor's instructions, and spanned the pH range from about 5.3 to about 6.3. Focussing was carried out for about 3 hours with application of from 1,000 to 4,000 volts (power between 1 and 4 watts). Fractions of 1 ml each were collected after focussing, and the pH and PMT activity of each fraction was measured. Focussing and fraction collection were done at 4° C.

Figure 4:
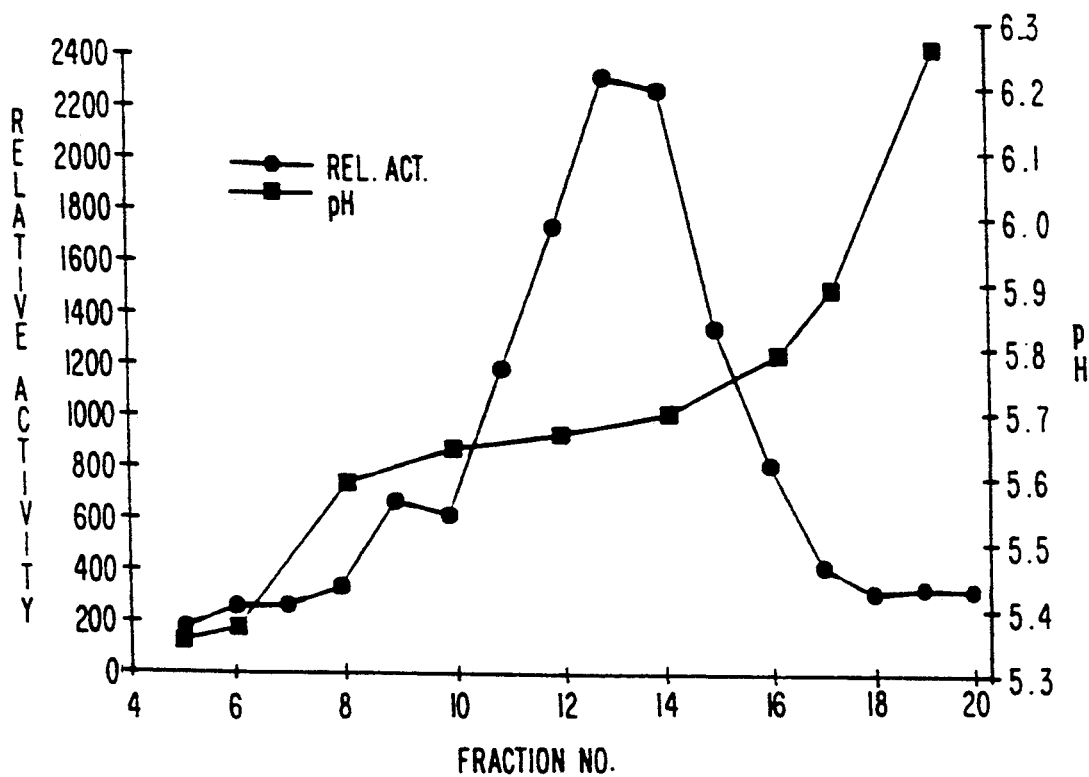
FIG. 4 is a graph depicting relative PMT activity and pH of fractions obtained by isoelectric focussing of tobacco PMT purified via ammonium sulfate fractionation, hydrophobic interaction chromatography, and putrescine elution from an anion exchange column followed by sample concentration. Enzymatic activity of PMT is expressed as $^{14}C$ disintegrations per minute (above background) recovered as product, and is designated "relative activity".

FIG. 4 is a dual plot of relative PMT activity and pH versus fraction number (i.e., location in the sucrose density gradient), after isoelectric focussing. The data from the experiment depicted in FIG. 4 indicated the isoelectric point of tobacco PMT to be approximately 5.7. In other isoelectric focussing experiments the pI of tobacco PMT appeared to be as low as 5.0 and as high as 5.8. Those of skill in the art will recognize that in practice, numerous factors affect apparent pI, and thus pI measurements normally exhibit some variation.

Assessment of Relative Purity of PMT

Relative purity of PMT at successive steps in the purification process was assessed by specific activity measurements (Table 1). The purification (fold) values shown in Table 1 are underestimates of the actual degree of purification from tobacco root crude extract, because the 40–65% ammonium sulfate fraction was taken as 100%, for activity yield calculations.

TABLE 1

| Process Stage | Total Protein (mg) | Specific Activity (units/mg) | Activity Yield (%) | Purification (fold) |
|---|---|---|---|---|
| Ammonium Sulfate | 4128* | 47.9 | 100.0 | 1.0 |
| Phenyl-Sepharose | 680 | 134.6 | 46.3 | 2.8 |
| DEAE/AHS | 1.76** | 5203 | 7.7** | 108.6 |

*Pool of 40–65% ammonium sulfate fractions from 4 separate crude extracts.
**Represents only half of material from phenyl-Sepharose column.

Relative purity of PMT at successive steps in the present process was also assessed by the standard procedure of SDS-PAGE. FIG. 1 shows SDS-PAGE protein band patterns displayed (upon silver staining) by samples at each of the steps in the PMT purification process. Samples on the gel were as follows: lanes 1 and 6, molecular weight standard proteins (listed above, in Brief Description of the Figures); lane 2, 40–65% ammonium sulfate fraction; lane 3, PMT activity peak fraction from phenyl-Sepharose column; lane 4, concentrated material from DEAE/AHS step; lane 5, PMT activity peak fraction from isoelectric focussing of concentrated material from DEAE/AHS step. It should be noted that the PMT band (indicated by arrow) that is prominent in the DEAE/AHS-purified material (lane 4) is barely visible in the material from the preceding hydrophobic interaction step (lane 3).

Molecular Weight of Tobacco PMT

The apparent molecular weight of tobacco PMT was measured in an experiment that involved isolation of PMT on a non-denaturing electrophoresis gel loaded with PMT material that had been through the ammonium sulfate, phenyl-Sepharose, and DEAE/AHS/ultrafiltration stages of purification. The non-denaturing stacking gel buffer contained 0.27 M Tris/HCl (pH 6.8), 10% (v/v) glycerol, and 20 mM 2-mercaptoethanol. The non-denaturing 12.5% polyacrylamide resolving gel buffer contained 0.38 M Tris/HCl (pH 8.8), 10% (v/v) glycerol, and 12 mM 2-mercaptoethanol.

A single lane from the non-denaturing gel was excised, cut in half along its length, and then cut into 3 mm slices. One half of each gel slice was placed directly into the standard PMT assay mixture, and the corresponding half of each gel slice was subjected to SDS-PAGE.

Figure 2:
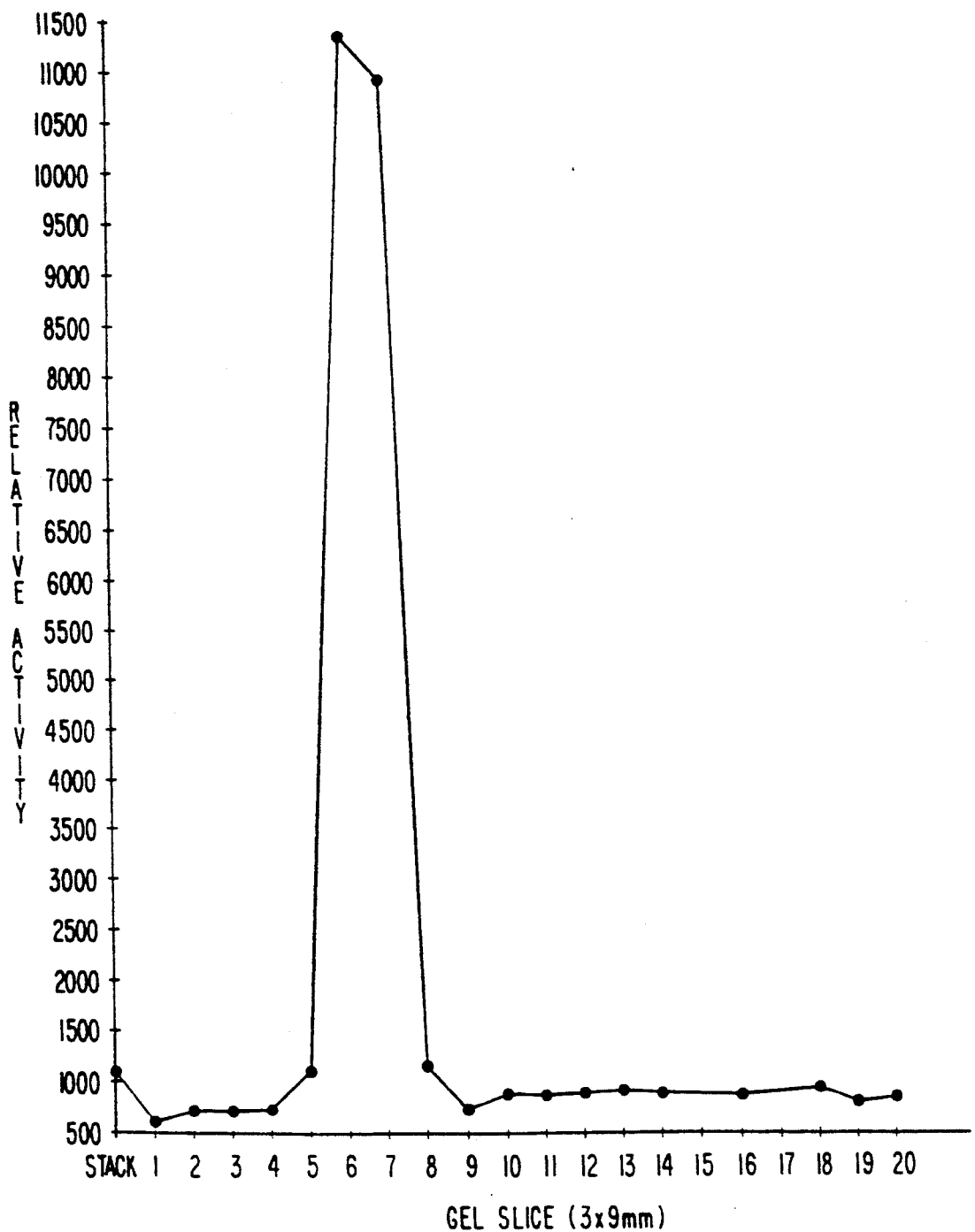
FIG. 2 is a graph depicting PMT activity in sequential 3 mm slices from a 12.5% non-denaturing polyacrylamide gel, onto which had been loaded concentrated putrescine-eluted material from an anion exchange column. Enzymatic activity of PMT is expressed as $^{14}C$ disintegrations per minute (above background) recovered as product, and designated "relative activity".
Figure 3:
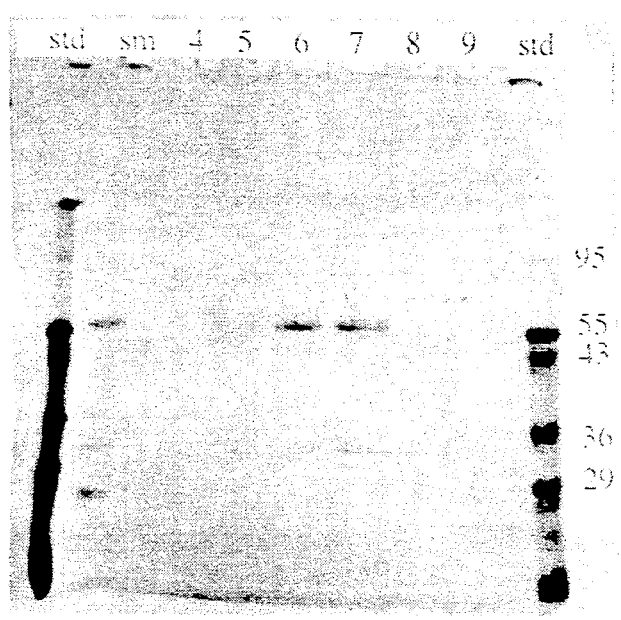
FIG. 3 is a reproduction of a photograph of a silver-stained 12.5% SDS-polyacrylamide gel on which successive 3 mm slices in and around the band of PMT activity on a non-denaturing electrophoresis gel (FIG. 2) were analyzed for purity and apparent molecular weight. Lane designated "sm" contains starting material (i.e., material applied to the non-denaturing gel). Lanes designated "std" contain molecular weight standard proteins (phosphorylase B, 95.5 kD; glutamate dehydrogenase, 55.0 kD; ovalbumin, 43.0 kD; lactate dehydrogenase, 36.0 kD, carbonic anhydrase, 29.0 kD; lactoglobulin, 18.4 kD; cytochrome C, 12.4 kD).

The non-denaturing gel slice that displayed the highest PMT activity (FIG. 2) contained essentially a single protein with an apparent molecular weight of about 60 kD (FIG. 3).

Enzymatic Activity of PMT

Substrate specificity tests were carried out with highly purified tobacco PMT of the present invention. 1,3-Diaminopropane and 1,5-diaminopentane (chemical analogs of putrescine), phosphatidylethanolamine (a methyl group acceptor), and N-methylputrescine (the normal product of PMT), were compared with putrescine (1,4-diaminobutane) for ability to serve as a substrate for PMT. When 1,3-diaminopropane, 1,5-diaminopentane, and the phosphatidylethanolamine were substituted for putrescine in the standard PMT assay (described above), no detectable amount of radioactive product was formed. When N-methylputrescine was substituted for putrescine in the PMT assay, radioactive product formation was less than 6% of that observed with putrescine.

Apparent $K_m$ values for the two PMT substrates, putrescine and S-adenosylmethionine, were determined by measuring PMT activity (as described above) at various rate-limiting concentrations of one substrate, while the other substrate was present in excess. The $K_m$ of partially purified tobacco PMT for putrescine was about 400 μM. The $K_m$ of highly purified tobacco PMT for S-adenosylmethionine was about 125 μM. The $K_m$ values found for putrescine, with partially purified tobacco PMT, and for S-adenosylmethionine, with highly purified tobacco PMT, agree closely with published values for PMT (Mizusaki et al., supra; Feth et al., "Determination Of Putrescine N-methyltransferase By High Performance Liquid Chromatography", *Phytochemistry*, 24, pp. 921–23 (1985)).

Amino-Terminal Amino Acid Sequence Analysis

Tobacco PMT for sequence analysis was isolated via SDS-PAGE of material that had been subjected to the purification steps of ammonium sulfate fractionation, phenyl-Sepharose chromatography, DEAE-Sepharose chromatography with putrescine elution (followed by concentration via AHS and ultrafiltration), and free-flow isoelectric focussing. Following SDS-PAGE of the highly purified PMT, the protein bands were electroblotted onto a polyvinylidene difluoride membrane ("Immobilon-P", Millipore, Bedford, MA) and visualized with amido black, by standard procedures. The piece of membrane bearing the "a1" band (see FIG. 5), which was one of only two bands in the highly purified preparation displaying a molecular weight characteristic of tobacco PMT (see FIG. 3), was cut out so as to avoid the adjacent "a2" band. The PMT thus isolated was subjected to amino terminal amino acid sequence analysis on an Applied Biosystems model 477A with an on-line 120A analyzer (pulse liquid phase sequencer), according to the manufacturer's recommended procedures.

The sequence of the first 17 amino acids at the amino terminus of the tobacco PMT "a1" band was found to be (SEQ ID NO:1): Leu Ser Xaa Asn Phe Leu Phe Gly Thr Ala Ser Ser Xaa Tyr Gln Tyr Glu.

The "a2" band (see FIG. 5) was the second of only two bands displaying the molecular weight of tobacco PMT (see FIG. 3). When the "a2" band (FIG. 5) was prepared and analyzed in the same manner as the "a1" band, the "a2" band yielded the following partial amino acid sequence (SEQ ID NO:2): Leu Ser Ser Asn Phe Leu Phe Gly Thr Ala Ala Pro Tyr Tyr Gln Tyr Glu.

While we have described a number of embodiments of this invention, it is apparent that our basic constructions can be altered to provide other embodiments which utilize the processes and products of this invention. Therefore, it will be appreciated that the scope of this invention is to be defined by the appended claims rather than by the specific embodiments which have been presented by way of example.

We claim:

1. A process for purifying putrescine N-methyltransferase from a tobacco plant extract comprising the steps of:
   (1) applying the extract to a solid phase anion exchange medium, wherein the application temperature and the pH and chemical composition of the extract are such that putrescine N-methyltransferase is retained by the anion exchange medium;
   (2) selectively eluting the putrescine N-methyltransferase from the anion exchange medium with an elution buffer comprising an effective amount of a polyamine selected from the group consisting of putrescine, N-methylputrescine, spermine, spermidine, agmatine, cadaverine, and mixtures thereof, wherein the elution temperature and the pH and chemical composition of the elution buffer are such that the putrescine N-methyltransferase would be retained by the anion exchange medium if the polyamine were not present; and
   (3) obtaining the purified putrescine N-methyltransferase in the eluate, wherein:
      (a) the application temperature is between about 2° C. and 10° C.;
      (b) the application pH is between about 7.2 and 8.3;
      (c) the effective amount of the polyamine is a concentration between about 0.5 and 50 mM;
      (d) the elution temperature is between about 18° and 26° C.; and
      (e) the elution pH is between about 7.2 and 8.3.

* * * * *

SEQUENCE LISTING ( 1 ) GENERAL INFORMATION:

(i) APPLICANT: Nakatani, Herbert Y.
                  Malik, Vedpal S.

(ii) TITLE OF INVENTION: PUTRESCINE N-METHYLTRANSFERASE, RECOMBINANT
                           DNA MOLECULES ENCODING PUTRESCINE
                           N-METHYLTRANSFERASE, AND TRANSGENIC TOBACCO
                           PLANTS WITH ALTERED NICOTINE CONTENT ( i i i ) NUMBER OF SEQUENCES: 3

(iv) CORRESPONDENCE ADDRESS:
         (A) ADDRESSEE: FISH & NEAVE
         (B) STREET: 875 Third Avenue
         (C) CITY: New York
         (D) STATE: New York
         (E) COUNTRY: U.S.A.
         (F) ZIP: 10022

(v) COMPUTER READABLE FORM:
         (A) MEDIUM TYPE: Floppy disk
         (B) COMPUTER: IBM PC compatible
         (C) OPERATING SYSTEM: PC-DOS/MS-DOS
         (D) SOFTWARE: PatentIn Release #1.24

(vi) CURRENT APPLICATION DATA:
         (A) APPLICATION NUMBER:
         (B) FILING DATE:
         (C) CLASSIFICATION:

(viii) ATTORNEY/AGENT INFORMATION:
         (A) NAME: Creason, Gary L.
         (B) REGISTRATION NUMBER: 34,310
         (C) REFERENCE/DOCKET NUMBER: PM-1412

(ix) TELECOMMUNICATION INFORMATION:
         (A) TELEPHONE: (212) 715-0600
         (B) TELEFAX: (212) 715-0674
         (C) TELEX: 14-8367

( 2 ) INFORMATION FOR SEQ ID NO:1:

( i ) SEQUENCE CHARACTERISTICS:
         ( A ) LENGTH: 17 amino acids
         ( B ) TYPE: amino acid
         ( D ) TOPOLOGY: linear ( i i ) MOLECULE TYPE: protein ( i i i ) HYPOTHETICAL: N ( v ) FRAGMENT TYPE: N-terminal ( v i ) ORIGINAL SOURCE:
         ( A ) ORGANISM: Nicotiana tabacum (B) STRAIN: Burley 21
(F) TISSUE TYPE: root (xi) SEQUENCE DESCRIPTION: SEQ ID NO:1:

Leu Ser Xaa Asn Phe Leu Phe Gly Thr Ala Ser Ser Xaa Tyr Gln Tyr
1               5                   10                  15

Glu (2) INFORMATION FOR SEQ ID NO:2:

(i) SEQUENCE CHARACTERISTICS:
    (A) LENGTH: 17 amino acids
    (B) TYPE: amino acid
    (D) TOPOLOGY: linear (ii) MOLECULE TYPE: protein (iii) HYPOTHETICAL: N (v) FRAGMENT TYPE: N-terminal (vi) ORIGINAL SOURCE:
    (A) ORGANISM: Nicotiana tabacum
    (B) STRAIN: Barley 21
    (F) TISSUE TYPE: Root (xi) SEQUENCE DESCRIPTION: SEQ ID NO:2:

Leu Ser Ser Asn Phe Leu Phe Gly Thr Ala Ala Pro Tyr Tyr Gln Tyr
1               5                   10                  15

Glu (2) INFORMATION FOR SEQ ID NO:3:

(i) SEQUENCE CHARACTERISTICS:
    (A) LENGTH: 17 amino acids
    (B) TYPE: amino acid
    (D) TOPOLOGY: linear (ii) MOLECULE TYPE: protein (iii) HYPOTHETICAL: N (v) FRAGMENT TYPE: N-terminal (vi) ORIGINAL SOURCE:
    (A) ORGANISM: Nicotiana tabacum
    (B) STRAIN: Barley 21
    (F) TISSUE TYPE: Root (xi) SEQUENCE DESCRIPTION: SEQ ID NO:3:

Leu Ser Xaa Asn Phe Leu Phe Gly Thr Ala Xaa Xaa Xaa Tyr Gln Tyr
1               5                   10                  15

Glu